United States Patent [19]

Mayhew et al.

[11] Patent Number: 6,051,600
[45] Date of Patent: *Apr. 18, 2000

[54] LIPOSOMAL HYDROLYSIS-PROMOTING HYDROPHOBIC TAXANE DERIVATIVES

[76] Inventors: Eric Mayhew, 26 Allison Ct.; Shaukat Ali, 27 Jamie Ct., both of Monmouth Junction, N.J. 08852; Andrew S. Janoff, 560 Countess Dr., Yardley, Pa. 19067

[ * ] Notice: This patent is subject to a terminal disclaimer.

[21] Appl. No.: 08/805,184

[22] Filed: Feb. 27, 1997

Related U.S. Application Data

[63] Continuation-in-part of application No. 08/712,684, Sep. 12, 1996, Pat. No. 5,703,117
[60] Provisional application No. 60/003,575, Sep. 12, 1995.

[51] Int. Cl.$^7$ ...................... A61K 31/335; C07D 305/14
[52] U.S. Cl. ........................... 514/449; 549/510; 549/511
[58] Field of Search ............................ 514/449; 549/510, 549/511

[56] References Cited

U.S. PATENT DOCUMENTS

| | | | |
|---|---|---|---|
| 4,235,871 | 11/1980 | Papahadjopoulos et al. | 424/19 |
| 4,522,803 | 6/1985 | Lenk et al. | 424/1.1 |
| 4,588,578 | 5/1986 | Fountain et al. | 424/1.1 |
| 4,837,028 | 6/1989 | Allen | 424/450 |
| 4,920,016 | 4/1990 | Allen et al. | 424/450 |
| 4,960,760 | 10/1990 | Stella et al. | 514/449 |
| 4,975,282 | 12/1990 | Cullis et al. | 424/450 |
| 5,008,050 | 4/1991 | Cullis et al. | 264/4.3 |
| 5,013,556 | 5/1991 | Woodle et al. | 424/450 |
| 5,015,744 | 5/1991 | Holton | 549/510 |
| 5,030,453 | 7/1991 | Lenk et al. | 424/450 |
| 5,059,699 | 10/1991 | Kingston et al. | 549/511 |
| 5,077,056 | 12/1991 | Bally et al. | 424/450 |
| 5,169,637 | 12/1992 | Lenk et al. | 424/450 |
| 5,200,534 | 4/1993 | Rao | 549/510 |
| 5,278,324 | 1/1994 | Kingston et al. | 549/510 |
| 5,534,499 | 7/1996 | Ansell | 514/25 |

FOREIGN PATENT DOCUMENTS

| | | | |
|---|---|---|---|
| 0 414 610 | 2/1991 | European Pat. Off. | C07C 233/83 |
| 0 522 958 | 1/1993 | European Pat. Off. | C07D 305/14 |
| 0 528 729 | 2/1993 | European Pat. Off. | C07C 269/06 |
| 91/13053 | 9/1991 | WIPO | C07C 229/34 |
| 93/06079 | 4/1993 | WIPO | C07C 228/10 |
| 93/10076 | 5/1993 | WIPO | C07C 231/20 |
| 93/16059 | 8/1993 | WIPO | C07D 305/14 |

OTHER PUBLICATIONS

Bangham, et al., "Diffusion of univalent Ions across the Lamellae of Swollen Phospholipids" J. Mol. Biol. 13:238–252, 1965.

Blume, et al., "Specific targeting with poly(ethylene glycol)–modified liposomes: coupling of homing devices to ends of thr polymeric chains compbines effective target binding with long circulation times", BBA 1149:180 (1993).

Borman, "Scientists Mobilize to Increase Supply of Anticancer Drug Taxol", Chemical & Engineering News, Sep. 2, 1991, p. 11–18.

Deamer, et al., Liposome Preparation: Methods and Mechanisma,. in *Liposomes* (M. Ostro, ed.,)Marcel Dekker, Inc., New York, (1983), pp. 27–52.

Edgington, "Taxol, out of the words", Biotechnology 9:933–938 (Oct. 1991).

Gabizon, et al., "Prologation of the Circulation Time of Doxorubicin Encapsulated in Liposomes Containing a Polytheylene Glyco–Derivatized Phospholipid: Pharmacokinetc Studies in Rodents and Dogs", Pharm Res., 10(5):703 (1993).

Holton, et al., "First Total Synthesis of Taxol. 1. Functionalization of the B Ring", J. Am. Chem. Sos. 116:1597–1600, (1994).

Narin, "Solutions, Emulsions, suspensions and Extractives" in:*Remington's Pharmacetuical Science* (A. Gennaro, ed.,) Mack Publishing Co., Easton, PA (1985), pp. 1492–1517.

Nicolau, "Design, systhesis and biological activity of pro-taxols", Nature, 364, 464–466, 1993.

Nicolau, "Total synthesis of taxol", Nature, 367 (1994) 630–634.

Park et al., "Some negatively charged phospholipid derivatives prolong the liposome circulation in vivo", BBA 1108:257 (1992).

Rizzo, et al., "Analysis of anitcancer drugs in biological gluids: determination of taxol with application to clinical pharmacodinetics", J. Pharm & Biomed. Anal, 8(2):159–164 (1990).

Schiff, et al., "Promotion of microtubule assembly in vitro by taxol", Nature 277:665 (1979).

Suffness, Antitumor Alkaloids, in: "The Alkalodis, vol. XXV", Academic Press, Inc. (1985), Chapter 1, pp. 6–18.

The Pharmacological Basis of Therapeutics (Goodman Filman, et al., eds.,) Pergamon press, New York (1990), p. 1239.

*Primary Examiner*—Ba K. Trinh

[57] ABSTRACT

Provided herein is a taxane having a hydrocarbon attached at the 2' and/or 7 positions, the hydrocarbon's alpha position being occupied by a "hydrolysis-promoting group" ("HPG"). Substitution of an HPG for the methylene unit ordinarily occupying the alpha position allows for enhanced in vivo hydrolysis of the hydrocarbon-taxane bond, and hence, for enhanced taxane therapeutic activity. Also provided herein are taxane-containing compositions, and methods of administering taxanes to animals, including those afflicted with cancers.

10 Claims, 1 Drawing Sheet

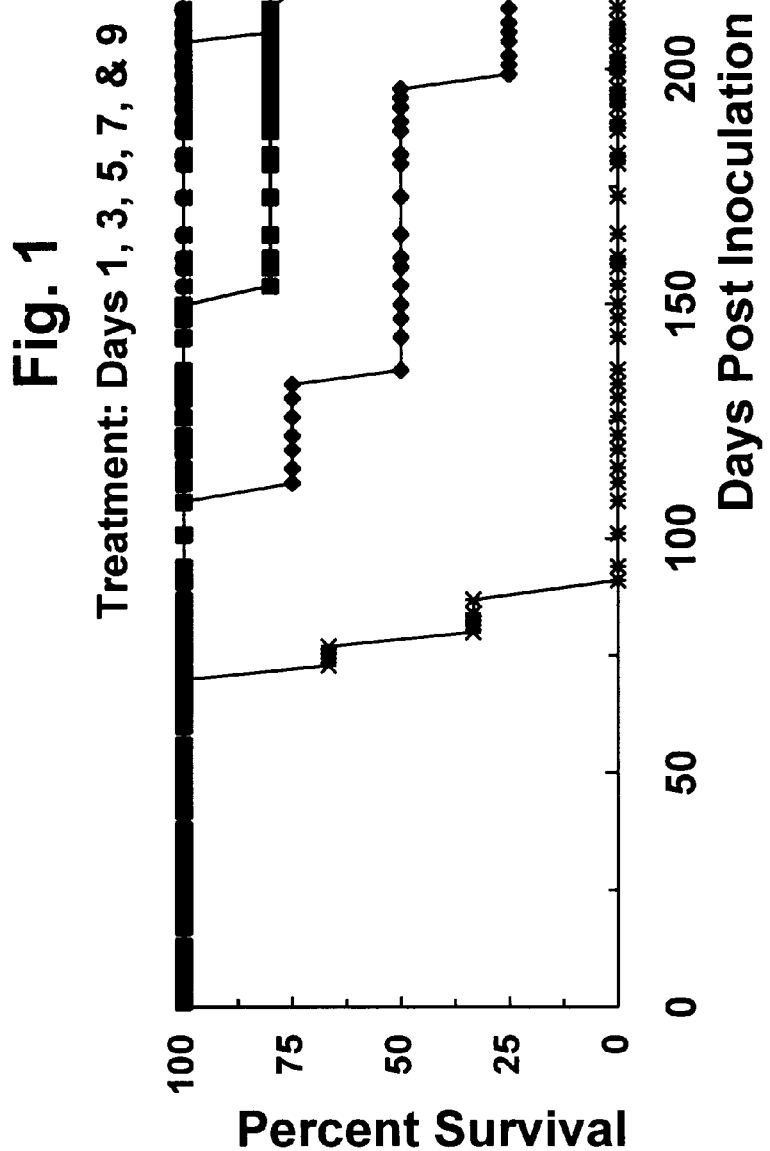

LIPOSOMAL HYDROLYSIS-PROMOTING HYDROPHOBIC TAXANE DERIVATIVES

This application is a continuation-in-part of U.S. Ser. No. 08/712,684, filed Sep. 12, 1996 and now U.S. Pat. No. 5,703,117, which-in-turn claims priority to provisional application U.S. Serial No. 60/003,575, filed Sep. 12, 1995.

FIELD OF THE INVENTION

This invention provides compounds which are a taxane to which an acyl chain has been attached; the acyl chain has been derivatized by the attachment thereto of a hydrolysis-promoting group. Also provided herein are compositions comprising such compounds, including lipid carrier-containing pharmaceutical compositions, and methods of administering such compositions to animals, such as humans afflicted with cancers.

BACKGROUND OF THE INVENTION

Taxanes can be isolated from natural sources, and can also be prepared synthetically from naturally occurring precursors. Paclitaxel (TAXOL®, Bristol-Myers Squibb), for example, can be prepared from baccatin by attachment of protecting groups to the hydroxyl groups of baccatin that are to become the hydroxyl groups of paclitaxel, converting the precursor baccatin to paclitaxel, and then removing the protecting groups from the hydroxyl groups to obtain paclitaxel (see, e.g., WO93/10076, int. pub. date May 27, 1993; K. V. Rao, U.S. Pat. No. 5,200,534; R. A. Holton, U.S. Pat. No. 5,015,744; PCT/US92/07990; V. J. Stella and A. E. Mathew, U.S. Pat. No. 4,960,790; K. C. Nicolau, Nature 364 (1993), pp. 464–466; Nicolau, K. C. et al. Nature 367 (1994) pp.630–634; Holton, R. A., et al. J. Am. Chem. Soc. 116 (1994) pp. 1597–1600; WO93/16059, int. pub. date Aug. 19, 1993; EP 528,729, published Feb. 24, 1993; EP 522,958, published Jan. 13, 1993; WO91/13053, int. pub. date Sep. 5, 1991; EP 414,610, int. pub. date Feb. 27, 1991; the contents of these documents are incorporated herein by reference).

Taxanes can be used effectively to treat a variety of cancers. Paclitaxel, for example, has been found to have activity against ovarian and breast cancers, as well as against malignant melanoma, colon cancer, leukemias and lung cancer (see, e.g., Borman, Chemical & Engineering News, Sep. 2, 1991, pp. 11–18; The Pharmacological Basis of Therapeutics (Goodman Gilman et al., eds.), Pergamon Press, New York (1990), p. 1239; Suffness, Antitumor Alkaloids, in: "The Alkaloids, Vol. XXV," Academic Press, Inc. (1985), Chapter 1, pp. 6–18; Rizzo et al., J. Pharm. & Biomed. Anal. 8(2):159–164 (1990); and Biotechnology 9:933–938 (October, 1991). Paclitaxel acts against cancer cells by binding to tubulin in the cells nuclei, thereby blocking the disassembly of microtubules and consequently, inhibiting cell division (Schiff et al., Nature 277:665 (1979).

However, formulation of taxanes in therapeutically useful carriers, so as to enable the taxanes to be administered to animals, is made difficult by the nature of the taxane molecules, which can be poorly soluble in both aqueous and lipid carriers. Paclitaxel, for example, is currently supplied as an emulsion in a polyoxyethylated derivative of castor oil and ethanol CremophorEL® because of its lack of significant aqueous or lipid solubility. However, as the cremophor carrier can itself be toxic to animals, administration of the cremophor-based paclitaxel formulation generally entails premedication with other drugs, as well as a slow infusion of a large volume of the formulation, thus necessitating over night hospital stays and their attendant costs.

Compositions provided herein provide taxanes in the form of compounds which are taxanes to which an acyl chain has been attached. The acyl chain enhances the taxane's lipid solubility, such that the taxane can be stably associated with a lipid-based carrier, e.g., a liposome, for an extended period of time. The acyl chain itself has been derivatized by the attachment thereto of a hydrolysis-promoting group, which is a chemical moiety that promotes hydrolysis of the derivatized acyl chain from the parent taxane, once the taxane has been disassociated from the lipid-based carrier, so as to give the parent taxane in a therapeutically useful form.

The compounds provided herein can be administered to animals as such, or may be formulated together with a lipid-based carrier prior to administration. Such formulations enhance delivery of the taxane to its intended site of action in an animal.

SUMMARY OF THE INVENTION

This invention provides a taxane having the formula:

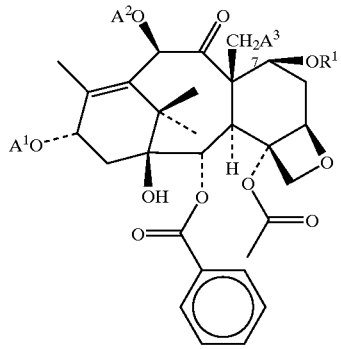

wherein: $A^1$ is H or a group having the formula $Z-C(O)NHCH(C_6H_5)CH(OR)C(O)-$; Z is $C_6H_5-$, $C_6H_5CH_2-O-$, $C(CH_3)_3-O-$ or $CH(CH_3)=C(CH_3)-$; $A^2$ is H or $CH_3C(O)-$; and $A^3$ is H or OH. Each of R and $R^1$ is H or a group having the formula $Y^1Y^2$, provided that at least one of R and $R^1$ is not H, and provided that when $A^3$ is H, $R^1$ is not H.

$Y^1$ is a group having the formula $-C(O)CHX^1(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}-$. The sum of $n1+2n2+n3+2n4+n5+2n6+n7+2n8n9$ is an integer of from 1 to 21, with each of n2, n4, n6 and n8 being independently zero or 1. n1 is equal to zero or an integer of from 1 to 21, n3 is equal to zero or an integer of from 1 to 18, n5 is equal to zero or an integer of from 1 to 15, n7 is equal to zero or an integer of from 1 to 12, n9 is equal to zero or an integer of from 1 to 9, and each of n1 to n9 can be the same or different at each occurrence. $Y^2$ is $-CH_3$, $-CO_2H$ or $-CH_2OH$.

$X^1$ is a hydrolysis promoting group ("HPG") including, but not limited to: F, Cl, Br, I, the group $—OC_6H_4X^2$ or the group $—C(O)X^2$, wherein $X^2$ is F, Cl, Br, I, $NH_3^+$, $NO_2$ or CN. Most preferably, $X^1$ is F, Cl, Br or I. Preferably, $A^1$ is the group $Z—C(O)NHCH(C_6H_5)CH(OR)C(O)—$; Z is preferably $C_6H_5$ and $A^1$ is more preferably the group $C_6H_5C(O)NHCH(C_6H_5)CH(OR)C(O)—$. Most preferably, $A^1$ is $C_6H_5C(O)NHCH(C_6H_5)CH(OR)C(O)—$, $A^2$ is $CH_3C(O)—$ and $A^3$ is H, that is, the taxane is a paclitaxel. When $R^1$ is a hydrogen, R is then $—Y^1Y^2$, and when R is a hydrogen, $R^1$ is $—Y^1Y^2$. The group $—Y^1Y^2$ preferably has the formula $—Y^1CH_3$, more preferably, the formula $—C(O)CHX^1(CH_2)_{n1}CH_3$; still more preferably, n1 is then 3, 5, 9, 11, 13 or 15.

Also provided herein are compositions comprising the taxane of this invention; such compositions can also comprise a pharmaceutically acceptable medium. The compositions preferably also comprises a lipid-based carrier, e.g., a fatty acid, phospholipid, lipoprotein, micelle, lipid complex or liposome, with which the taxane is associated so as to deliver the taxane to a site in the body where it can be therapeutically effective.

Preferably, the lipid carrier is a liposome, most preferably, a multilamellar liposome. The liposome preferably has a comprises a lipid component which comprises a saturated lipid, more preferably, a saturated phosphatidylcholine such as dimyristoyl phosphatidylcholine, dipalmitoyl phosphatidylcholine or distearoyl phosphatidylcholine. Most preferably, the saturated lipid is dimyristoyl phosphatidylcholine. The liposomal lipid component can consist essentially of a saturated lipid, e.g., dimyristoyl phosphatidylcholine. For taxanes associated with lipid carriers, the sum of n1+2n2+n3+2n4+n5+2n6n7+2n8+n9 is preferably an integer of from 3 to 21, more preferably an integer of from 9 to 21, and most preferably, an integer of from 13 to 21. That is, in compositions comprising taxanes associated with lipid carriers, the carrier has a lipid component comprising or consisting essentially of dimyristoyl phosphatidylcholine and the taxane is derivatized with a sixteen-carbon acyl chain.

Further provided herein is a method of administering a taxane to an animal, which comprises administering a taxane-containing composition of this invention to the animal. Preferably, the taxane thus administered is associated in the composition with a lipid carrier, more preferably, a liposome and most preferably, a multilamellar liposome. The animal can be afflicted with a cancer, e.g., a brain, stomach, lung, colon, prostate, breast or ovarian cancer, or a leukemia, lymphoma, carcinoma or sarcoma. Cancer treatment by this method involves administering an anticancer effective amount of a taxane to the affected animal. Typically, this anticancer effective amount of the taxane is from about 0.1 mg per kg of body weight of the animal to about 1000 mg per kg. For such anticancer treatment, the composition administered preferably contains a lipid carrier. Preferred anticancer taxanes are paclitaxels, i.e., taxanes wherein $A^1$ is $C_6H_5C(O)NHCH(C_6H_5)CH(OR)C(O)—$, $A^2$ is $CH_3C(O)—$ and $A^3$ is H. More preferably, R or $R^1$ is $—C(O)CHX^1(CH_2)_{n1}CH_3$, and most preferably, n1 is then 3, 5, 9, 11, 13 or 15. Furthermore, an additional bioactive agent can be administered to an animal as part of administration of a taxane to the animal.

BRIEF DESCRIPTION OF THE DRAWING

FIG. 1. Effect of Paclitaxel- and 2'-(2-Bromo) Hydrophobic Pacltaxel Derivative ("HTD")-Containing Liposomes on the Survival of OVCAR3 Tumor-Bearing SCID Mice. Filled diamonds: paclitaxel liposomes; filled squares: 2-bromo-C6 HTD (paclitaxel substituted with a 6-carbon acyl chain attached to paclitaxel's 2' hydroxyl group, the acyl chain having a bromine atom attached to its alpha carbon); filled triangles: 2-bromo-C8 HTD; open diamonds: 2-bromo-C12 HTD; open triangles: 2-bromo-C14 HTD; open circles: 2-bromo-C16 HTD; and, *: "empty" liposomes (liposomes not containing paclitaxel or a substituted paclitaxel derivative).

DETAILED DESCRIPTION OF THE INVENTION

This invention provides a taxane having the formula:

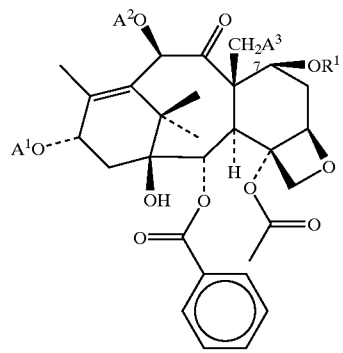

$A^1$ is H or a group having the formula $Z—C(O)NHCH(C_6H_5)CH(OR)C(O)—$, $A^2$ is H or $CH_3C(O)—$, and $A^3$ is H or OH. Z is $C_6H_5$, $C_6H_5CH_2—O—$, $C(CH_3)_3—O—$ or $CH(CH_3)=C(CH_3)—$. Mostly preferably, $A^1$ is $C_6H_5C(O)NHCH(C_6H_5)CH(OR)C(O)—$, $A^2$ is $CH_3C(O)—$ and $A^3$ is H. Accordingly, the taxane most preferred herein is a paclitaxel ([Compound I]; TAXOL® ($C_{47}H_{51}NO$), Bristol-Myers Squibb) derivative.

However, taxotere (II)-based derivatives, which differ from paclitaxel by having a tert-butoxy carbonyl group at the C-12 position, instead of a benzoyl group, and a hydroxyl group, instead of an acetyloxy group, at C-10 are also provided herein. Accordingly, for taxotere, $A^1$ is $C(CH_3)_3OC(O)NHCH(C_6H_5)CH(OR)C(O)—$, $A^2$ is H, and $A^3$ is H.

Further taxanes useful in accordance with the practice of this invention include, without limitation: Cephalomannine (III); 19-hydroxybaccatin III [IV], Baccatin V [V], 10-deacetyl cephalomannine [VI], 10-deacetyl paclitaxel [VII], 7-Epi-10-deacetyl paclitaxel [VIII], 7-Epi-10-deacetyl cephalomannine [IX], and 10-deacetyl baccatin III [X], as described in the following table.

| Compound | $A^1$ | $A^2$ | $A^3$ |
|---|---|---|---|
| Paclitaxel (I) | $C_6H_5C(O)NHCH(C_6H_5)CH(OR)C(O)$— | $CH_3C(O)$— | H |
| Taxotere (II) | $C(CH_3)_3OC(O)NHCH(C_6H_5)CH(OR)C(O)$— | H | H |
| Cephalomannine (III) | $(CH_3)CH=C(CH_3)C(O)NHCH(C_6H_5)CH(OR)C(O)$— | $CH_3C(O)$— | H |
| 19-hydroxybaccatin III (IV) | H | $CH_3C(O)$— | OH |
| Baccatin III (V) | H | $CH_3C(O)$— | H |
| 10-Deacetylcephalomannine (VI) | $(CH_3)CH=C(CH_3)C(O)NHCH(C_6H_5)CH(OR)C(O)$— | H | H |
| 10-Deacetyltaxol (VII) | $C_6H_5C(O)NHCH(C_6H_5)CH(OR)C(O)$— | H | H |
| (7α-OH)7-Epi-10-deacetyltaxol(7β-OH) (VIII) | $C_6H_5C(O)NHCH(C_6H_5)CH(OR)C(O)$— | H | H |
| 7-Epi-10-deacetylcephalomannine(7β-OH) (IX) | $(CH_3)CH=C(CH_3)C(O)NHCH(C_6H_5)CH(OR)C(O)$— | H | H |
| 10-Deacetylbaccatin III (X) | H | H | H |

Each of R and $R^1$ is H or a group having the formula —$Y^1Y^2$, provided that at least one of R and $R^1$ is not H and provided that when $A^3$ is H, $R^1$ is not H. $Y^1$ is the group —$C(O)CHX^1(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}$—. The sum of n1 +2n2+n3 +2n4+n5 +2n6+n7 +2n8+n9 is an integer of from 1 to 21, wherein each of n2, n4, n6 and n8 is independently zero or 1. n1 is equal to zero or an integer of from 1 to 21, n3 is equal to zero or an integer of from 1 to 18, n5 is equal to zero or an integer of from 1 to 15, n7 is equal to zero or an integer of from 1 to 12, and n9 is equal to zero or an integer of from 1 to 9. Each of n1 to n9 can be the same or different at each occurrence. Preferably, $Y^1$ is saturated, that is, there are no double bonds between adjacent carbon atoms. Accordingly, n2, n4, n6 and n8 are each preferably zero, n3, n5, n7 and n9 are each also zero, and $Y^1$ is preferably —$C(O)CHX^1(CH_2)_{n1}$—. Alternatively, $Y^1$ can be unsaturated, that is, it can have one or more double bonds and one or more CH=CH units; accordingly, at least one of n2, n4, n6 and n8 is then 1. For example, when the unsaturated acyl chain has one double bond: n2 is 1, n4, n6 and n8 each being zero; $Y^1$ is then —$C(O)CHX^1(CH_2)_{n1}CH=CH(CH_2)_{n3}$—; n1 is zero or an integer from 1 to 18; n3 is also zero or an integer from 1 to 18, at least one of n1 or n3 is not zero, and the sum of n1 plus n3 is equal to an integer of from 1 to 19.

$Y^2$ is preferably —$CH_3$, the acyl chain thus being derived from a monocarboxylic acid, but can also be —$CO_2H$, the acyl chain being derived from an omega dicarboxylic acid, or —$CH_2OH$, the acyl chain then being derived from an omega hydroxy acid. Accordingly, the group $Y^1Y^2$ preferably has the formula —$C(O)CHX^1(CH_2)_{n1}CH_3$, wherein n1 is most preferably equal to 3, 5, 9, 11 or 13, whether the group be located at R, $R^1$ or both R and $R^1$.

"Attachment" of the group —$Y^1Y^2$ to a taxane means forming a chemical connection between the group and the taxane by any means generally accepted in the art for forming such connections. Attachment is to one or more reactive groups, typically hydroxy groups, on the taxane. Attachment of any acyl chain to a taxane can stabilize the taxane-lipid carrier association, such that the taxane an carrier remain together, for example, in the plasma of animals for a longer period of time than does the corresponding acyl chain-free taxane. Increased stability of association enhances the amount of the taxane reaching its intended site of therapeutic action in vivo.

Paclitaxel, for example, has three hydroxyl groups to which acyl chains can be attached; these are located at the 1,2' and 7 positions, with their relative order of reactivity generally believed to be (from most reactive to least reactive) 2'>7>1. Hydrocarbons can be attached to the primary reactive group of a taxane, e.g., the 2' OH group of paclitaxel, utilizing stoichiometric amounts of the an active form of the acid, e.g., chlorides or anhydrides. The hydroxyl group at the 7 position of paclitaxel can be modified by attaching an acyl chain to both the 2' and 7 OH groups, and then selectively removing the 2' acyl chain so that the acyl chain at the 7 position remains attached to paclitaxel. Selective removal of the 2' acyl chain can be accomplished using stoichiometric amounts of a mild base, e.g., sodium bicarbonate. Additionally, the 7 OH group of paclitaxel can be modified by "protecting" the 2' OH group before covalently linking paclitaxel with the acyl chain. The 2' OH group can also be protected with groups such as, for example, triphenyl methyl, methoxytriphenyl methyl, trifluoroacetyl and TrOC (trichloromethoxy chloroformate) groups, using processes generally known to ordinarily skilled artisans. The protected paclitaxel is then reacted with an active form of the acyl chain, e.g., anhydrides or chlorides, in anhydrous organic solvent, and bases such as DMAP and pyridine. The protecting group can be removed from the 2' position by well known and readily practiced means, under mildly acidic or basic conditions; TrOC groups, for example, can be removed by zinc reduction reactions.

Reactions are typically performed in the presence of a base, such as pyridine, dimethylaminopyridine ("DMAP"), triethylamine, or others, and in common polar, aprotic organic solvents such as dimethyl formamide, dimethyl sulfoxide and the like. The progress of the reaction can be monitored by a number of well known chromatographic means, for example, thin layer chromatography using a 3% methanol-in-chloroform solvent system. The compound's identity can be confirmed by spectroscopic procedures, such as NMR spectroscopy.

For example, the following reaction scheme, and the information described below, can be used to prepare 2'-(±)-2-Bromoacyl paclitaxels:

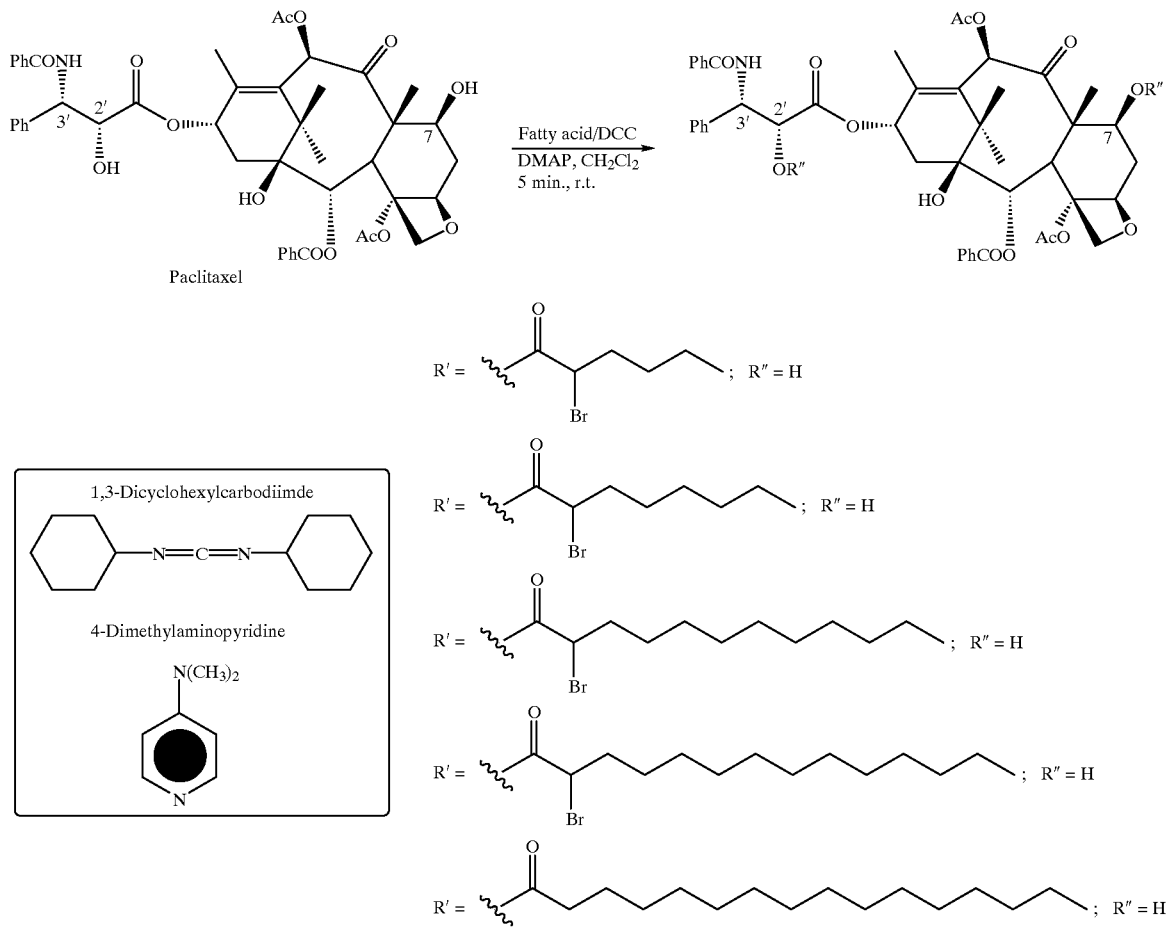

However, specific reaction and purification conditions are generally expected to vary according to a number of factors, including without limitation, the raw materials and reactants used, that are well within the purview of ordinarily skilled artisans to determine and control given the teachings of this invention.

Acyl chains substituted with a hydrolysis-promoting group on the alpha carbon can be purchased from commercially available sources, or synthesized according to any of the means generally accepted in the art for substitution of a hydrogen atom on the alpha carbon of a fatty acid.

"Hydrolysis-promoting-groups" ("HPGs") are substitutions at an acyl chain's alpha carbon (Cα) that promote hydrolysis of the bonds between a parent taxanes its attached acyl chain. HPGs are electronegative relative to hydrogen, meaning that they draw electrons to themselves more than a hydrogen atom would if it occupied the same position in the same molecule. Accordingly, substitution of a hydrolysis-promoting group for a hydrogen atom on the alpha carbon results in a redistribution of an acyl chain's electron density, and thereby causes an inductive effect in the acyl chain. Substitution of aromatic moiety-containing HPGs for alpha carbon-attached hydrogens can also cause resonance effects, these too involving electron density redistribution in the substituted acyl chain. HPG-induced induction and resonance effects stabilize an acid's corresponding base form, but not the acid itself, and thereby causes the acid to be a stronger acid than it would be if there was a $CH_2$ group in the acyl chain instead of the HPG. HPG-substituted acyl chains thus generally have lower $pK_a$'s than their corresponding native forms, that is, the form in which a $CH_2$ group is present at the alpha position instead of an HPG-substituted group, and hence, HPG-substituted acyl chains are more readily hydrolyzable from their parent taxanes than are nonsubstituted chains. Accordingly, the hydrolysis-promoting group $X^1$ can be any atom or group of atoms: (1) having an electronegativity greater than hydrogen; and, (2) that can be attached at the alpha position of an acyl chain. $X^1$ can, for example, be F, Cl, Br, I, $NH_3^+$, the group $—OC_6H_4X^2$ or the group $—C(O)X^2$; $X^2$ is, for example, F, Cl, Br, I, $NH_3^+$, $NO_2$ or CN. Preferably, $X^1$ is F, Cl, Br or I.

Also provided herein is a composition comprising a taxane of this invention. Compositions intended for therapeutic use of the taxane preferably comprise a pharmaceutically acceptable medium, which is a medium generally intended for use in connection with the administration of active ingredients, such as therapeutic or diagnostic agents, to animals. These include, without limitation: solids, such as pills, capsules and tablets; gels; excipients; and aqueous or nonaqueous solutions.

Pharmaceutically acceptable media are generally formulated according to a number of factors well within the purview of the ordinarily skilled artisan to determine and account for, including without limitation: the particular active ingredient used, its concentration, stability and intended bioavailability; the disease, disorder or condition being treated with the composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, J. G. Nairn, in: *Remington's Pharmaceutical Science* (A. Gennaro, ed.), Mack Publishing Co., Easton, Pa., (1985), pp. 1492–1517, the contents of which are incorporated herein by reference). Typical pharmaceutically acceptable media used in parenteral drug administration include, for example, D5W, an aqueous solution containing 5% weight by volume of dextrose, and physiological saline.

Taxane-containing pharmaceutical compositions provided herein preferably comprise a lipid carrier with which the taxane is associated. "Lipid carriers" are hydrophobic or amphipathic molecules suitable for administration to animals, and include, without limitation: fatty acids, phospholipids, micelles, lipoproteins, lipid complexes, i.e., nonliposomal, lipid-based structures which may, but are not required to contain one or more nonlipid components, and liposomes. Preferably, the lipid carrier is a liposome.

"Liposomes" comprise one or more bilayers of lipid molecules, each bilayer encompassing an aqueous compartment. Unilamellar liposomes have a single lipid bilayer, and multilamellar liposomes have more than one bilayer. The amphipathic lipid molecules which make up lipid bilayers comprise a polar (hydrophilic) headgroup and one or two acyl chains. The polar groups can be phosphate-, sulfate- or nitrogen-based groups, but are preferably phosphate groups, such as phosphorylcholine, phosphorylethanolamine, phosphorylserine, phosphorylglycerol or phosphorylinositol groups. The acyl chains generally comprise from 12 to 24 carbon atoms, and can be saturated (e.g., lauric, myristic, palmitic, or stearic acid), or unsaturated (e.g., oleic, linoleic, linolenic, or arachidonic acid). Liposomal lipid can also include sterols, such as cholesterol, and other lipids.

Liposomes can be made by a variety of methods, including: Bangham's methods for making multilamellar liposomes (MLVs) involving drying of a lipid/organic solvent solution and then rehydrating the dried lipids with an aqueous solution (see Bangham et al., 1965); Lenk's, method for making MLVs with substantially equal interlamellar solute distribution (SPLVs) involving forming a biphasic mixture of an aqueous phase and a lipid-containing organic phase, and then emulsifying the lipid in the aqueous phase while evaporating the organic (see U.S. Pat. Nos. 4,522,803, 5,030,453, and 5,169,637); Fountain's (U.S. Pat. No. 4,588,578) method of making SPLVs using a monophasic solvent system; Cullis' (U.S. Pat. No. 5,008,050) method of making SPLVs using repeated cycles of freezing and thawing; preparation of REVs through formation of a water-in-oil emulsion, from which the organic phase is evaporated to give a gel, the gel then being agitated to give oligolamellar liposomes (see Papahadjopoulos et al., U.S. Pat. No. 4,235, 871); extrusion of MLVs to make unilamellar liposomes (see, e.g., Cullis et al., U.S. Pat. No. 4,975,282); as well as sonication or homogenization of larger liposomes, or ether or ethanol injection processes (see, for example, R. Deamer and P. Uster, "Liposome Preparation: Methods and Mechanisms," in *Liposomes* (M. Ostro, ed.), Marcel Dekker, Inc., New York (1983), pp. 27–52). The contents of these liposome preparation documents are incorporated herein by reference.

More preferably, the liposome is a multilamellar liposome. The liposome preferably has a lipid component which comprises a saturated lipid; the lipid component can consist essentially of the saturated lipid. The saturated lipid is preferably a phosphatidylcholine such as dimyristoyl phosphatidylcholine, dipalmitoyl phosphatidylcholine and distearoyl phosphatidylcholine. More preferably, the phosphatidylcholine is dimyristoyl phosphatidylcholine. Taxanes associated with lipid carriers in pharmaceutical compositions preferably have an acyl chain which is at least six carbon atoms long, more preferably at least twelve carbon atoms long, and most preferably, at least 16 carbon atoms long; the acyl chain is preferably saturated.

Most preferably, the lipid carrier is a multilamellar liposome having a lipid component which comprises or consists essentially of dimyristoyl phosphatidylcholine, and the taxane is derivatized with a sixteen carbon-long saturated acyl chain having a bromine atom at the alpha carbon.

"Association" as used herein generally means association between the acyl chain attached to the taxane and the hydrophobic portion of the lipid carrier. Without intending to be limited by theory, it is believed that such association is by way of a number of influences, such as Van der Waal's forces, generally known to operate between hydrophobic molecules in an aqueous environment. Means of determining the stability of such associations, for example, by determining the percentage of taxane recoverable with phosphorous when the lipid carrier comprises a phospholipid are readily practiced by ordinarily skilled artisans given the teachings of this invention.

Lipid carriers associated with the taxane of this invention can comprise an additional bioactive agent, that is, a bioactive agent in addition to the taxane. Lipid carrier/bioactive agent formulations can enhance the therapeutic index of the bioactive agent, for example by buffering the agent's toxicity and by reducing the rate at which the agent is cleared from the circulation of animals, thereby meaning that less of the agent need be administered to achieve the desired therapeutic effect. "Bioactive agents" are compounds or compositions of matter having biological activity on animal cells in vitro or when administered to an animal; bioactive agents can have therapeutic and/or diagnostic activity. Such agents include, but are not limited to, antimicrobial, anti-inflammatory and anticancer agents as well as radioactive isotopes, enzymes and dyes. Additional bioactive agents also include bioactive lipids, such as certain ceramides and ether lipids, which themselves have therapeutically beneficial properties. Preferably, the additional bioactive agent is an anticancer agent.

Lipid carriers can also comprise one or more "headgroup-modified lipids." These comprise polar groups derivatized by attachment thereto of a moiety which can inhibit the binding of serum proteins to headgroup-modified lipid-containing lipid carriers. This alters the pharmacokinetic behavior of the carriers such that they remain in circulation longer (see, e.g., Blume et al., Biochim. Biophys. Acta. 1149:180 (1993); Gabizon et al., Pharm. Res. 10(5):703 (1993); Park et al. Biochim. Biophys Acta. 1108:257 (1992); Woodle et al., U.S. Pat. No. 5,013,556; Allen et al., U.S. Pat. Nos. 4,837,028 and 4,920,016; the contents of these documents being incorporated herein by reference).

Headgroup-modified lipids are typically phosphatidylethanolamines (PE's), for example dipalmitoyl phosphatidylethanolamine ("DPPE"), palmitoyloleoyl phosphatidylethanolamine ("POPE") and dioleoyl phosphatidylethanolamine ("DOPE"), amongst others. Such lipids have headgroups generally derivatized with organic dicarboxylic acids, such as succinic or glutaric acid ("GA"), or their corresponding anhydrides.

The amount of the headgroup-modified lipid incorporated into the lipid carrier generally depends upon a number of factors well known to the ordinarily skilled artisan, or within his purview to determine without undue experimentation. These include, but are not limited to: the type of lipid and the type of headgroup modification; the type and size of the carrier; and the intended therapeutic use of the formulation. Typically, from about 5 mole percent to about 20 mole percent of the lipid in a headgroup-modified lipid-containing lipid carrier is headgroup-modified lipid.

Further provided herein is a method of administering a taxane to an animal, which comprises administering the composition of this invention to the animal, preferably a mammal such as a human. Administration is by any other means generally accepted for administration of therapeutic agents to animals, but is preferably intravenous or intraperitoneal. Animals afflicted with cancers can be treated by therapeutic administration of taxane-containing compositions, wherein the compositions comprise an anticancer effective amount of a taxane.

Generally, those cancers treatable by this method are those which are, or may be, treated with the corresponding free taxane, i.e., a taxane not having an attached acyl chain. These include, without limitation: brain, breast, colon, lung, ovarian, prostate, pancreatic and stomach cancers; as well as, leukemias, lymphomas, sarcomas and carcinomas. Preferably, the treated cancer is a breast or ovarian cancer. The cancer treated can be a cancer that is resistant to standard therapeutic regimens, i.e., a drug-resistant cancer.

A taxane's anticancer activity can be determined by examining the taxane's ability to inhibit the growth of cells in vitro, for example, by incubating a cancer cell culture with the derivative, and then evaluating cell growth inhibition in the culture. Alternatively, a taxane can be tested in vivo for antitumor activity, for example, by first establishing tumors in suitable test animals, e.g., immune-deficient mice such as SCID mice, administering the taxane to the animals and then measuring tumor growth inhibition and survival rates. Cells suitable for such in vitro or in vivo testing include, without limitation: murine P388 leukemia, B16 melanoma and Lewis lung cancer cells; human breast carcinoma MCF7, human MCF-7/ADR (adriamycin-resistant), human ovarian OVCAR-3, human HT-29 colon carcinoma and A549 human lung carcinoma cells; and other cells generally accepted in the art for such testing, including those cells which are drug-resistant. Ordinarily skilled artisans given the teachings of this invention are well able to select particular taxanes for application against certain cancers, on the basis of such factors as $GI_{50}$, $ED_{50}$, survival rates and other data derived from routine in vitro or in vivo experimentation "Anticancer effective amounts" of a taxane are any amount of the taxane effective to ameliorate, lessen, inhibit or prevent the establishment, growth, metastasis, invasion or spread of a cancer, and can be the same amount as therapeutic doses of the corresponding free taxane. However, the attachment of an HPG-derivatized acyl chain to a taxane and the association of this taxane with a lipid carrier can enhance the taxane's therapeutic index. Thus, anticancer effective amounts of this derivatized acyl chain-taxane can also be less than those of the corresponding free taxane. Taxane anticancer effective amounts can be chosen in accordance with a number of factors, e.g., the age, size and general condition of the subject, the cancer being treated and the intended route of administration of the derivative, and determined by a variety of means, for example, dose ranging trials, well known to, and readily practiced by, ordinarily skilled artisans given the teachings of this invention. Generally, the anticancer effective amount of the taxane is at least about 0.1 mg of the taxane per kg of body weight of the animal to which the taxane-containing composition is administered. Typically, the anticancer effective amount of the taxane is from about 0.1 mg per kg of body weight of the animal to about 1000 mg per kg; preferably, the anticancer effective amount is from about 1 mg per kg to about 200 mg per kg.

Preferably, taxane-containing compositions provided herein also comprise a lipid carrier, more preferably, a liposome and most preferably a unilamellar liposome having a diameter of less than about 200 nm. Preferred anticancer taxanes have A being the group $C_6H_5C(O)NHCH(C_6H_5)CH(OR)C(O)$—, $A^2$ being $CH_3C(O)$— and $A^3$ being H, i.e., are paclitaxels. At least one of R or $R^1$ is preferably —C(O)CHX$^1$(CH$_2$)$_3$CH$_3$, —C(O)CHX$^1$(CH$_2$)$_5$CH$_3$, —C(O)CHX$^1$(CH$_2$)$_9$CH$_3$, —C(O)CHX$^1$(CH$_2$)$_{11}$CH$_3$ or —C(O)CHX$^1$(CH$_2$)$_{13}$CH$_3$, with $X^1$ preferably being F, Cl, Br or I.

Tables 3 and 4 (below) present results showing the acute toxicity of paclitaxel or the paclitaxel derivative in the mice, that is, the number of mice in each treatment group that died within the first 14 days post-injection. The results show that both of the paclitaxel derivative-containing liposomes were less toxic than were the paclitaxel-containing liposomes, with all five of the mice in the group receiving 100 mg per kg paclitaxel dying within the first 14 days. 2-Bromo-C16 paclitaxel (paclitaxel to which a sixteen-carbon acyl chain has been attached at the 2' position, the acyl chain being derivatized by the substitution of a bromine atom for an alpha carbon hydrogen atom) derivative-containing liposomes were less toxic than were the 2-bromo-C6 paclitaxel derivative-containing liposomes. Tables 3 and 4 (below) present results showing the acute toxicity of paclitaxel or the paclitaxel derivative in the mice, that is, the number of mice in each treatment group that died within the first 14 days post-injection. The results show that both of the paclitaxel derivative-containing liposomes were less toxic than were the paclitaxel-containing liposomes, with all five of the mice in the group receiving 100 mg per kg paclitaxel dying within the first 14 days. 2-Bromo-C16 paclitaxel derivative (paclitaxel derivatized with a 16-carbon hexanoyl chain to which has been attached a bromine atom on the alpha carbon)-containing liposomes were less toxic than were the 2-bromo-C6 paclitaxel derivative-containing liposomes. Moreover, liposomes containing either paclitaxel or a 2'(2-bromo)hydrophobic paclitaxel derivative (containing either a six-carbon (C-6), C-8, C-12, C-14 or C-16 acyl chain at the 2' position) were administered, intraperitoneally in 5 doses, to scid (severe combined immunodeficiency) mice bearing a human ovarian cancer (OvCar 3), at a dose of 12.5 m paclitaxel per kg or a dose of 50 paclitaxel derivative per kg. Results of this treatment are presented in FIG. 1, in terms of days of mouse survival post administration of either paclitaxel or a paclitaxel derivative. These results clearly show that treatment with a paclitaxel derivative extended the life span of the mice, in comparison to treatment either with paclitaxel itself or with an 'empty" liposome, i.e., a liposome containing neither paclitaxel or a paclitaxel derivative. Moreover, paclitaxel derivatives having acyl chains of increasing length were increasingly effective at extending life spans.

Furthermore, an additional bioactive agent can be administered to the animal as part of this invention's method; the additional agent is preferably, but not necessarily, a component of the taxane-containing composition, and is preferably, but not necessarily, associated with the lipid carrier when the composition contains such a carrier. Preferably, that carrier is a liposome. Liposomes can be loaded with bioactive agents by solubilizing the agent in the lipid or aqueous phase used to prepare the liposomes. Alternatively, ionizable bioactive agents can be loaded into liposomes by first forming the liposomes, establishing an electrochemical potential, e.g., by way of a pH gradient, across the outermost liposomal bilayer, and then adding the ionizable agent to the aqueous medium external to the liposome (see Bally et al. U.S. Pat. No. 5,077,056, the contents of which are incorporated herein by reference).

This invention will be better understood from the following Examples. However, those of ordinary skill in the art will readily understand that these examples are merely illustrative of the invention as defined in the claims which follow thereafter.

EXAMPLES

Example 1

Preparation of 2'-(±)-2-Bromohexanoyl taxol 2'-(±)-2-Bromo octanoyl, dodecanoyl, tetradecanoyl, and hexadecanoyl paclitaxels were prepared (in 80–90% yield) by the procedure explained below, and identified by the $^1$H NMR and elemental analysis. To a 10 min. stirred solution of (±)-2-bromohexanoic acid (229 mg, 1.17 mmol) and 1,3-dicyclohexyl carbodiimide (241 mg, 1.17 mmol) in 30 ml of dry methylene chloride, was added taxol (500 mg, 0.586 mmol) and the base 4-dimethylaminopyridine (71.5 mg, 0.586 mmol). The reaction mixture was allowed to proceed at room temperature for 5 min. The white precipitate of dicyclohexyl urea was filtered through a Celite pad. The resultant filtrate was evaporated under vacuo and the residue obtained was purified by a preparative thin layer chromatography in $CHCl_3$:MeOH (95:5) to give the desired product ($R_f$=0.58 in $CHCl_3$:MeOH, 95:5). After passing through a Metricel filter (0.1 m) to remove the silica gel from the $CHCl_3$ solution, the product was lyophilized from cyclohexane to give 507 mg (84% yield) as the white powder.

$^1$H NMR ($CDCl_3$, 300 MHz) chemical shifts of some of the characteristic peaks at δ (in ppm): 8.14 (d, J=7.3 Hz, 2H, aromatic), 7.72( d, J=7.3 Hz, 2H, aromatic), 7.61 (m, 1H, aromatic), 7.54–7.48 (m, 3H, aromatic), 7.42–7.36 (m, 7H, aromatic), 6.87 (dd, J=2.4 Hz, 3,4 Hz, 1H, NH), 6.29 (m, 2H, H-10 and H-13), 6.0 (m, 1H, H-3')5.68 (d, J=6.9 Hz, 1H, H-2b), 5.50 (dd, J=1.4 Hz, 1.0 Hz, 1H, H-2'), 4.97 (d, J=7.8 Hz, 1H, H-5), 4.45 (m, 1H, H-7), 4.32 (d, J=7.3 Hz, 1H, H-20a), 4.28 (m, 1H, CH(Br)), 4.20 (d, J=8.3 Hz, 1H, H-20b), 4.0 (br, OH), 3.81 (d, J=6.9 Hz, 1H, H-3), 0.86 (app. t. 3H, w-$CH_3$). FABMS: ($MH^+$) calcd for $C_{53}H_{60}NO_{15}Br$ 1029.32. Found 1030.

Scheme I: Route to the synthesis of 2'-(±)-2-Bromoacyl paclitaxels ("DCC"=1,3-dicyclohexylcarbodiimide' "DMAP"=4-dimethylaminopyridine)

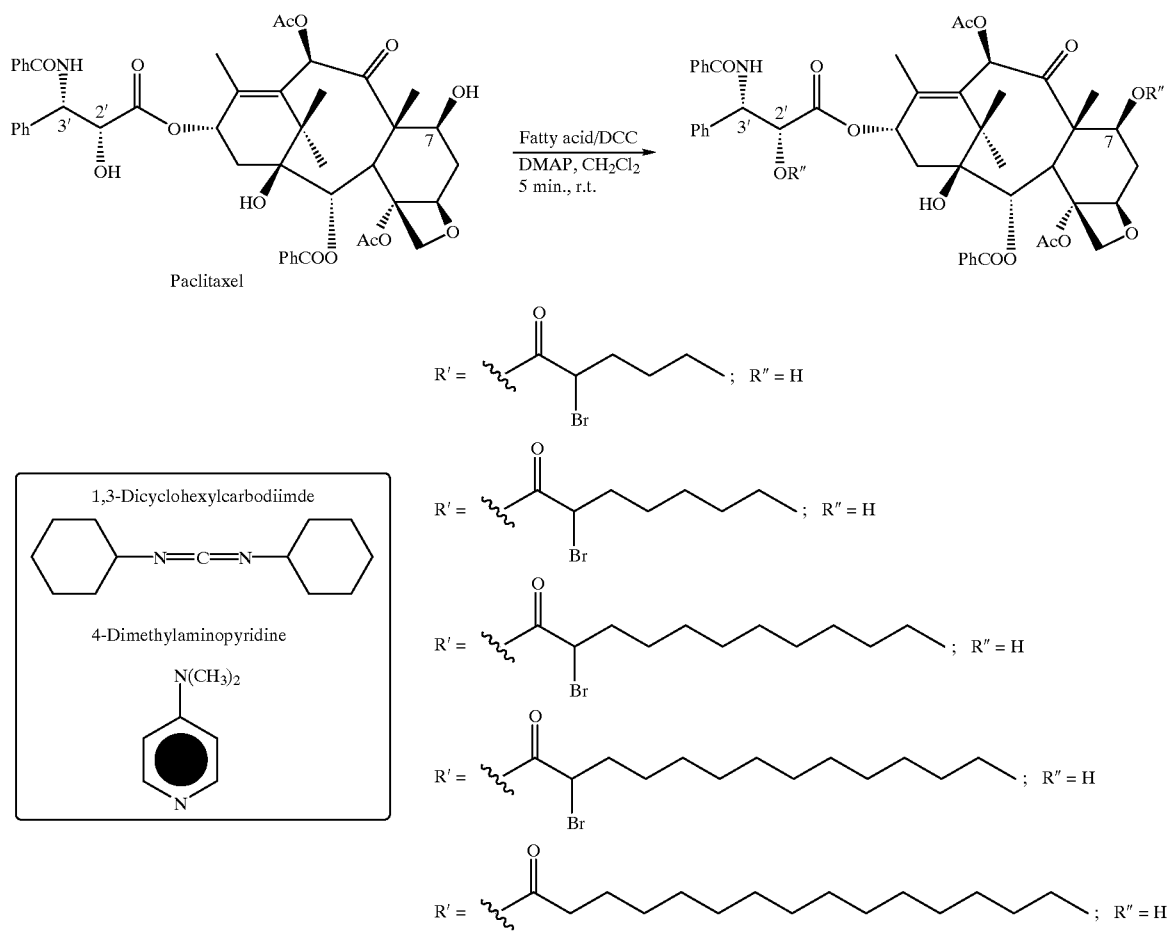

Example 2

In Vitro Studies

Table 1 (see below) shows the $GI_{50}$ ($\mu$M) values (±standard deviation), that is, the concentration required for 50% Growth Inhibition, of various hydrolyzable taxane derivatives (HTDs) and human MCF-7 breast carcinoma cells following a 72-hour incubation of the cells with the HTD.

TABLE 1

| HTD CYTOTOXICITY | |
| --- | --- |
| Paclitaxel Derivative | $GI_{50}$ |
| 2'-Hexanoyl— | 0.500 ± 0.151 |
| 2'-2-Bromohexanoyl— | 0.003 ± 0.0002 |
| 2'-6-Bromohexanoyl— 7-Hexanoyl— | >10.000 0.027 ± 0.019 |
| 7-2-Bromohexanoyl— | 0.0046 ± 0.0001 |
| 7-6-Bromohexanoyl— | 0.018 ± 0.002 |
| 2'-Acetyl-7-Hexanoyl— | 4.46 ± 0.06 |

TABLE 1-continued

| HTD CYTOTOXICITY | |
| --- | --- |
| Paclitaxel Derivative | $GI_{50}$ |
| 2',7-di-2-Bromohexanoyl— 2',7-diHexanoyl— | 1.43 ± 0.72 >10.00 |
| 2'-Troc-7-2-Bromohexanoyl— | 2.67 ± 0.08 |
| 2'-Troc-7-6-Bromohexanoyl— | 0.47 ± 0.03 |

"2'" indicates attachment of an acyl chain to paclitaxel at the 2' position;
"7'": attachment at the 7' position;
"bromo": derivatization of an attached acyl chain with a bromine atom.

Table 2 (see below) shows the $GI_{50}$ ($\mu$M) values, averaged from two separate experiments (SRB standard cytotoxicity assay), for paclitaxel and various 2'-2-bromo paclitaxel derivatives and A-549 human lung carcinoma, MCF-7 human breast carcinoma, MCF-7/ADR (adriamycin-resistant) and HT-29 human colon carcinoma cells following a 72-hour incubation of the cells and HTDs ("C-6, 8, 12, 14 and 16": 6, 8, 12, 14 and 16-carbon acyl chains, respectively, attached to paclitaxel).

TABLE 2

In Vitro Sensitivity

| HTD | A-549 | MCF-7 | MCF-7/ADR | HT-29 |
|---|---|---|---|---|
| Paclitaxel | 0.0023 ± 0.0002 | <0.0015 | 4.1675 ± 0.7177 | <0.0014 |
| 2'-2-Bromo-C6-Paclitaxel | 0.0039 ± 0.0008 | 0.0023 ± 0.0013 | >10.0000 | 0.0024 ± 0.0009 |
| 2'-2-Bromo-C8-Paclitaxel | 0.0044 ± 0.0001 | 0.0029 ± 0.0010 | >10.0000 | 0.0031 ± 0.0003 |
| 2'-2-Bromo-C12-Paclitaxel | 0.0044 ± 0.0001 | 0.0028 ± 0.0007 | >10.0000 | 0.0032 ± 0.0002 |
| 2'-2-Bromo-C14-Paclitaxel | 0.0317 ± 0.0047 | 0.0160 ± 0.0091 | >10.0000 | 0.0206 ± 0.0057 |
| 2'-2-Bromo-C16-Paclitaxel | 0.1273 ± 0.0356 | 0.0710 ± 0.0373 | >10.0000 | 0.0595 ± 0.0187 |

Example 3

In Vivo Studies

CDF1 female mice, 5 or 10 mice per group, were intraperitoneally administered either paclitaxel-, 2'-C6-paclitaxel derivative-, or 2'-C16-paclitaxel derivative-containing liposomes, in a single doses, of either 12.5, 25, 50, 100, 200, 300, 400 or 500 mg of paclitaxel or paclitaxel derivative per kg of mouse body weight. Tables 3 and 4 (below) present results showing the acute toxicity of paclitaxel or the paclitaxel derivative in the mice, that is, the number of mice in each treatment group that died within the first 14 days post-injection. The results show that both of the paclitaxel derivative-containing liposomes were less toxic than were the paclitaxel-containing liposomes, with all five of the mice in the group receiving 100 mg per kg paclitaxel dying within the first 14 days. 2-Bromo-C16 paclitaxel derivative-containing liposomes were less toxic than were the 2-bromo-C6 paclitaxel derivative-containing liposomes.

TABLE 3

SINGLE DOSE ADMINISTRATION

| | | Paclitaxel Derivative | |
|---|---|---|---|
| Dose (mg/kg) | Paclitaxel | 2-Bromo-C6 | 2-Bromo-C16 |
| 500 | — | 5/5 | 0/5 |
| 400 | — | 5/5 | 1/5 |
| 300 | — | 4/5 | 1/5 |
| 200 | — | 0/2 | — |
| 100 | 5/5 | — | — |
| 50 | 0/10 | — | — |
| 25 | 0/10 | — | — |
| 12.5 | 0/10 | — | — |

TABLE 4

FIVE DOSE ADMINISTRATION

| Dose (mg/kg) | Paclitaxel | 2-Bromo-C6 Paclitaxel Derivative |
|---|---|---|
| 50 | 10/10 | 0/5 |
| 25 | 10/10 | — |
| 12.5 | 0/10 | — |

Liposomes containing either paclitaxel or a 2'-(2-bromo) hydrophobic paclitaxel derivative (containing either a six-carbon (C-6), C-8, C-12, C-14 or C-16 acyl chain at the 2' position) were administered, intraperitoneally in 5 doses, to scid (severe combined immunodeficiency) mice bearing a human ovarian cancer (OvCar 3), at a dose of 12.5 m paclitaxel per kg or a dose of 50 paclitaxel derivative per kg. Results of this treatment are presented in FIG. 1, in terms of days of mouse survival post administration of either paclitaxel or a paclitaxel derivative. These results clearly show that treatment with a paclitaxel derivative extended the life span of the mice, in comparison to treatment either with paclitaxel itself or with an 'empty" liposome, i.e., a liposome containing neither paclitaxel or a paclitaxel derivative. Moreover, paclitaxel derivatives having acyl chains of increasing length were increasingly effective at extending life spans.

What is claimed is:

1. A liposome which comprises:
   (i) a lipid component comprising a saturated acyl chain lipid;
   (ii) a taxane having the formula:

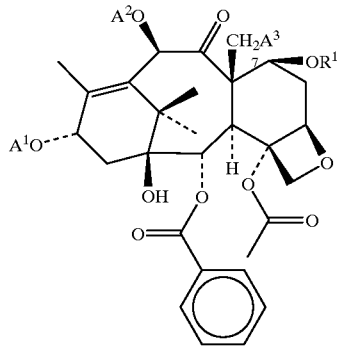

wherein:
$A^1$ is H or a group having the formula Z—C(O)NHCH($C_6H_5$)CH(OR)—C(O)—;
Z is $C_6H_5$—, $C(CH_3)_3$—O— or $CH(CH_3)$=$C(CH_3)$—;
$A^2$ is H or $CH_3C(O)$—;
each of R and $R^1$ is H or a group having the formula $Y^1Y^2$, provided that at least one of R and $R^1$ is not H and provided that when $A^1$ is H or when $A^1$ is Z—C(O)NHCH($C_6H_5$)CH(OR)—C(O)— and R is H, $R^1$ is not H;
$Y^1$ is —C(O)CHX$_1$($CH_2$)$_{n1}$(CH=CH)$_{n2}$($CH_2$)$_{n3}$(CH=CH)$_{n4}$($CH_2$)$_{n5}$(CH=CH)$_{n6}$($CH_2$)$_{n7}$(CH=CH)$_{n8}$($CH_2$)$_{n9}$;
the sum of n1+2n2+n3+2n4+n5+2n6+n7+2n8+n9 is an integer of from 1 to 21, n1 is zero or an integer of from 1 to 21, each of n2, n4, n6 and n8 is independently zero or 1, n3 is zero or an integer of from 1 to 18, n5 is zero or an integer of from 1 to 15, n7 is zero or an integer of from 1 to 12, n9 is zero or an integer of from 1 to 11 and n1 to n9 can be the same or different at each occurrence;
$X^1$ is an hydrolysis-promoting group; and $Y^2$ is $CH_3$, $CO_2H$ or OH.

2. The liposome of claim 1 which is a multilamellar liposome.

3. The liposome of claim 2, wherein the multilamellar liposome has substantially equal interlamellar solute distribution.

4. The liposome of claim 1, wherein the saturated acyl chain lipid is a phosphatidylcholine selected from the group consisting of dimyristoyl phosphatidylcholine, dipalmitoyl phosphatidylcholine and distearoyl phosphatidylcholine.

5. The liposome of claim 1, wherein $A^1$ is a group having the formula $C_6H_5C(O)NHCH(C_6H_5)CH(OH)$—$C(O)$—R and wherein $A^2$ is $CH_3C(O)$—.

6. The liposome of claim 5, wherein $R^1$ is H and R is —$C(O)CHX^1(CH_2)_3CH_3$, —$C(O)CHX^1(CH_2)_5CH_3$, —$C(O)CHX^1(CH_2)_9CH_3$, —$C(O)CHX^1(CH_2)_{11}CH_3$, —$C(O)CHX^1(CH_2)_{13}CH_3$ or —$C(O)CHX^1(CH_2)_{15}CH_3$.

7. The liposome of claim 6, wherein $X^1$ is Br.

8. The liposome of claim 5, wherein R is H and $R^1$ is —$C(O)CHX^1(CH_2)_3CH_3$, —$C(O)CHX^1(CH_2)_5CH_3$, —$C(O)CHX^1(CH_2)_9CH_3$, —$C(O)CHX^1(CH_2)_{11}CH_3$, —(O)CHX^1(CH_2)_{13}CH_{13}$ or —$C(O)CHX^1(CH_2)_{15}CH_3$.

9. The liposome of claim 8, wherein $X^1$ is Br.

10. The liposome of claim 1, comprising: a phosphatidylcholine selected from the group consisting of dimyristoyl phosphatidylcholine, dipalmitoyl phosphatidylcholine and distearoyl phosphatidylcholine; and, a taxane wherein $R^1$ is H and R is —$C(O)CHBr(CH_2)_3CH_3$, —$C(O)CHBr(CH_2)_5CH_3$, —$C(O)CHBr(CH_2)_9CH_3$, —$C(O)CHBr(CH_2)_{11}CH_3$, —(O)CHX^1(CH_2)_{13}CH_3$ or —$C(O)CHBr(CH_2)_{15}CH_3$, or wherein R is H and $R^1$ is —$C(O)CHBr(CH_2)_3CH_3$, —$C(O)CHBr(CH_2)_5CH_3$, —$C(O)CHBr(CH_2)_9CH_3$, —$C(O)CHBr(CH_2)_{11}CH_3$, —(O)CHX^1(CH_2)_{13}CH_3$ or —$C(O)CHBr(CH_2)_{15}CH_3$.

* * * * *

UNITED STATES PATENT AND TRADEMARK OFFICE
CERTIFICATE OF CORRECTION

PATENT NO : 6,051,600      Page 1 of 5

DATED : April 18, 2000

INVENTOR(S) : Mayhew et al.

It is certified that error appears in the above-identified patent and that said Letters Patent are hereby corrected as shown below:

Columns 7-8, delete the " OR " group at the 2' position of the right-most compound and substitute therefore --OR'--

Columns 7-8, "5 min" in the synthesis formula, should read --15 min--.

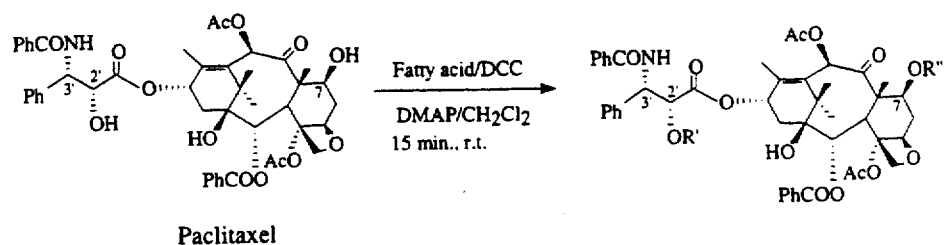

UNITED STATES PATENT AND TRADEMARK OFFICE
CERTIFICATE OF CORRECTION

PATENT NO : 6,051,600        Page 2 of 5
DATED      : April 18, 2000
INVENTOR(S) : Mayhew et al It is certified that error appears in the above-identified patent and that said Letters Patent are hereby corrected as shown below:

Columns 7-8, the 5th acyl chain formula should have a "Br" group at the acyl chain's alpha carbon.

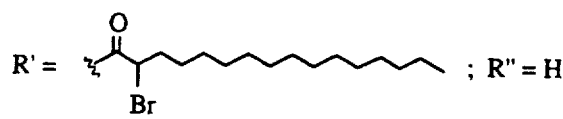

Columns 7-8, in the formula for 4 dimethylaminopyridine, the ring shown with a filled in black circle should show 3 double bonds.

4-Dimethylaminopyridine (DMAP)

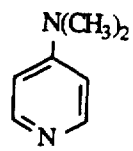

UNITED STATES PATENT AND TRADEMARK OFFICE
CERTIFICATE OF CORRECTION

PATENT NO : 6,051,600   Page 3 of 5
DATED : April 18, 2000
INVENTOR(S) : Mayhew et al It is certified that error appears in the above-identified patent and that said Letters Patent are hereby corrected as shown below:

Columns 15-16, delete the " OR" " group at the 2' position of the right-most compound and substitute therefore --OR'--.

Columns 15-16, "5 min" in the synthesis formula, should read --15 min--.

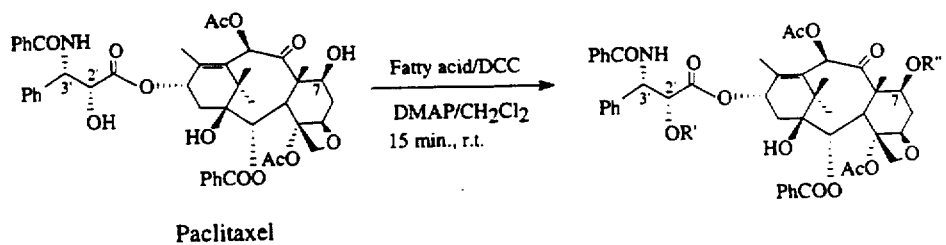

Paclitaxel

UNITED STATES PATENT AND TRADEMARK OFFICE
CERTIFICATE OF CORRECTION

PATENT NO : 6,051,600

DATED : April 18, 2000

INVENTOR(S) : Mayhew et al

It is certified that error appears in the above-identified patent and that said Letters Patent are hereby corrected as shown below:

Columns 15-16, the 5th acyl chain formula should have a "Br" group at the acyl chain's carbon.

Columns 15-16, in the formula for 4-dimethylaminopyridine, the ring shown with a filled in black circle should show 3 double bonds.

4-Dimethylaminopyridine (DMAP)

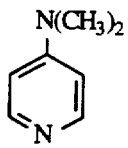

UNITED STATES PATENT AND TRADEMARK OFFICE
CERTIFICATE OF CORRECTION

PATENT NO : 6,051,600

DATED : April 18, 2000

INVENTOR(S) : Mayhew et al

It is certified that error appears in the above-identified patent and that said Letters Patent are hereby corrected as shown below:

Columns 16, line 59, insert --acyl-- between "bromo and paclitaxel".

Signed and Sealed this

Twenty-second Day of May, 2001

NICHOLAS P. GODICI

Attest:

Attesting Officer

Acting Director of the United States Patent and Trademark Office